United States Patent
Patch et al.

(10) Patent No.: US 7,878,976 B2
(45) Date of Patent: Feb. 1, 2011

(54) METHOD AND SYSTEM OF THERMOACOUSTIC IMAGING WITH EXACT INVERSION

(75) Inventors: Sarah K. Patch, Milwaukee, WI (US); David Finch, Corvallis, OR (US); Victor Palamodov, Karlsruhe (DE)

(73) Assignees: General Electric Company, Schenectady, NY (US); Ramot At Tel Aviv Univ, Ltd., Tel-Aviv (IL); Oregon State University, Corvallia, OR (US)

( * ) Notice: Subject to any disclaimer, the term of this patent is extended or adjusted under 35 U.S.C. 154(b) by 1943 days.

(21) Appl. No.: 10/864,567

(22) Filed: Jun. 9, 2004

(65) Prior Publication Data

US 2005/0277834 A1    Dec. 15, 2005

(51) Int. Cl.
*A61B 8/00* (2006.01)
(52) U.S. Cl. ............... 600/438; 378/4; 600/407; 600/425
(58) Field of Classification Search ............ 378/4; 600/407, 438, 425
See application file for complete search history.

(56) References Cited

U.S. PATENT DOCUMENTS

| 5,761,346 | A | * | 6/1998 | Moody | 382/254 |
| 6,005,916 | A | * | 12/1999 | Johnson et al. | 378/87 |
| 6,216,025 | B1 | * | 4/2001 | Kruger | 600/407 |
| 2006/0039525 | A1 | * | 2/2006 | Bontus et al. | 378/4 |

OTHER PUBLICATIONS

Xu et al. ("Reconstructions in limited-view thermoacoustic tomography", Med. Phys. 31 (4), Apr. 2004).*

Xu et al., Time-domain Reconstruction for Thermoacoustic Tomography in a Spherical Geometry, Jul. 2002, IEEE Transactions on Medical Imaging, vol. 21, No. 7, pp. 814-822.*

* cited by examiner

*Primary Examiner*—Long V Le
*Assistant Examiner*—Ellsworth Weatherby
(74) *Attorney, Agent, or Firm*—Ziolkowski Patent Solutions Group, SC

(57) ABSTRACT

The present invention is directed to a method and system of TCT imaging whereupon an exact inversion formula is used for reconstruction of TCT data. The present invention utilizes inversion formulae that are of the filtered backprojection and ρ-filter types.

23 Claims, 3 Drawing Sheets

METHOD AND SYSTEM OF THERMOACOUSTIC IMAGING WITH EXACT INVERSION

BACKGROUND OF THE INVENTION

The present invention relates generally to diagnostic imaging and, more particularly, to a method and system of thermoacoustic computed tomography (TCT) with exact inversion of TCT data for image reconstruction.

It is generally well known that wave propagation and integral geometry are the physical and mathematical underpinnings of most diagnostic imaging modalities. To date, most of these standard modalities have been predicated upon the measurement of the same type of output energy as was input to the system. For example, ultrasound diagnostic systems transmit and receive ultrasonic waves and, from those ultrasonic waves, are capable of generating a diagnostic image. CT systems are predicated upon the transmission and reception of x-ray or gamma ray radiation. In conventional CT systems, x-rays are projected toward an imaging subject and the attenuation of those x-rays caused by the subject is measured and processed to reconstruct a diagnostically valuable and probative image of the subject. Recently, however, hybrid imaging or diagnostic systems have been developed along with associated imaging techniques whereupon the measured output energy is different in form and type from the energy input to the system.

For instance, thermoacoustic tomography (TCT) is predicated upon and uses radio frequency (RF) energy projected at an imaging subject and measures emitted ultrasonic waves resulting from the application of the RF energy. Near infrared radiation is also non-ionizing and may also be used to heat tissue. TCT imaging involves the measurement of ultrasonic signals that are induced in the tissue of a subject whenever pulsed or continuous application of radiation is absorbed within the tissue, and the detection of resulting ultrasonic signals with transducers placed on or outside the imaging subject. More particularly, the ultrasonic transducers placed about the subject detect shock waves that are created in tissue when RF energy is absorbed and cause a heating and expansion of tissue. For example, it is known that cancerous masses absorb more RF energy than healthy tissue. As such, cancerous masses preferentially absorb RF energy, heat, and expand more quickly than neighboring healthy tissue thereby creating a shock wave which, when detected by an ultrasonic transducer, allows for detection of, or contrast between, cancerous or abnormal tissues and healthy tissues. Therefore, assuming a constant sound speed, the sound or ultrasonic waves, detected at any point in time after application of the RF energy, are generated by inclusions or abnormal masses lying on a sphere of radius $c\Delta t$ where $\Delta t$=time delta between RF input and received signal centered at a particular transducer. Standard reflection ultrasound assumes constant soundspeed. Because this assumption is correct to within a few percent, the surfaces of integration are nearly spherical.

Known TCT relies upon an inexact inversion solution to generate a reconstruction data set. This inexactitude of the reconstruction data can therefore affect image quality and, ultimately, the diagnostic value of the reconstructed image. More precisely, standard reconstruction method used in TCT is filtered backprojection with xray CT weights and kernel, even though such a method is not exact for TCT.

It would therefore be desirable to design a method and system of TCT imaging whereupon the acquired TCT data is reconstructed via a mathematically exact method.

BRIEF DESCRIPTION OF THE INVENTION

The present invention is directed to a method and system of TCT imaging whereupon a complete data set is used to reconstruct an image that overcomes the aforementioned drawbacks. To generate an exact reconstruction, the present invention utilizes inversion formulas that are of the filtered backprojection or $\rho$-filter type. In this regard, the present invention utilizes a weighting operator that is used to weight the acquired TCT data before application of an adjoint such that the resulting image is less susceptible to reconstruction errors.

Therefore, the present invention includes a method of diagnostic imaging which includes the steps of acquiring TCT data and determining an adjoint of the TCT data. The method further includes determining a weighting operator and modifying the TCT data by the adjoint and the weighting operator to generate a reconstruction data set. The method further includes the step of reconstructing an image of the subject from the reconstruction data set.

In accordance with another aspect of the present invention, a TCT imaging system includes an energy source configured to apply energy to an imaging object to induce thermal expansion in the imaging object. One or more sensors is provided to acquire ultrasonic data from the imaging object caused by energy induced thermal expansion in the imaging object. The imaging system further includes a computer programmed to apply an exact inversion to the acquired ultrasonic data According to another aspect of the present invention, a computer readable storage medium has a computer program stored thereon and represents a set of instructions that when executed by a computer causes the computer to acquire ultrasonic data resulting from application of energy to cause thermal induced displacement in an imaging object. The computer is further caused to determine an adjoint from the ultrasonic data. The computer is then caused to weight the acquired ultrasonic data by a weighting operator to form a weighted set of ultrasonic data. The adjoint is then applied to the weighted set of ultrasonic data to form a final set of ultrasonic data. The set of instructions then causes the computer to reconstruct an image from the final set of ultrasonic data by applying a high-pass filter.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
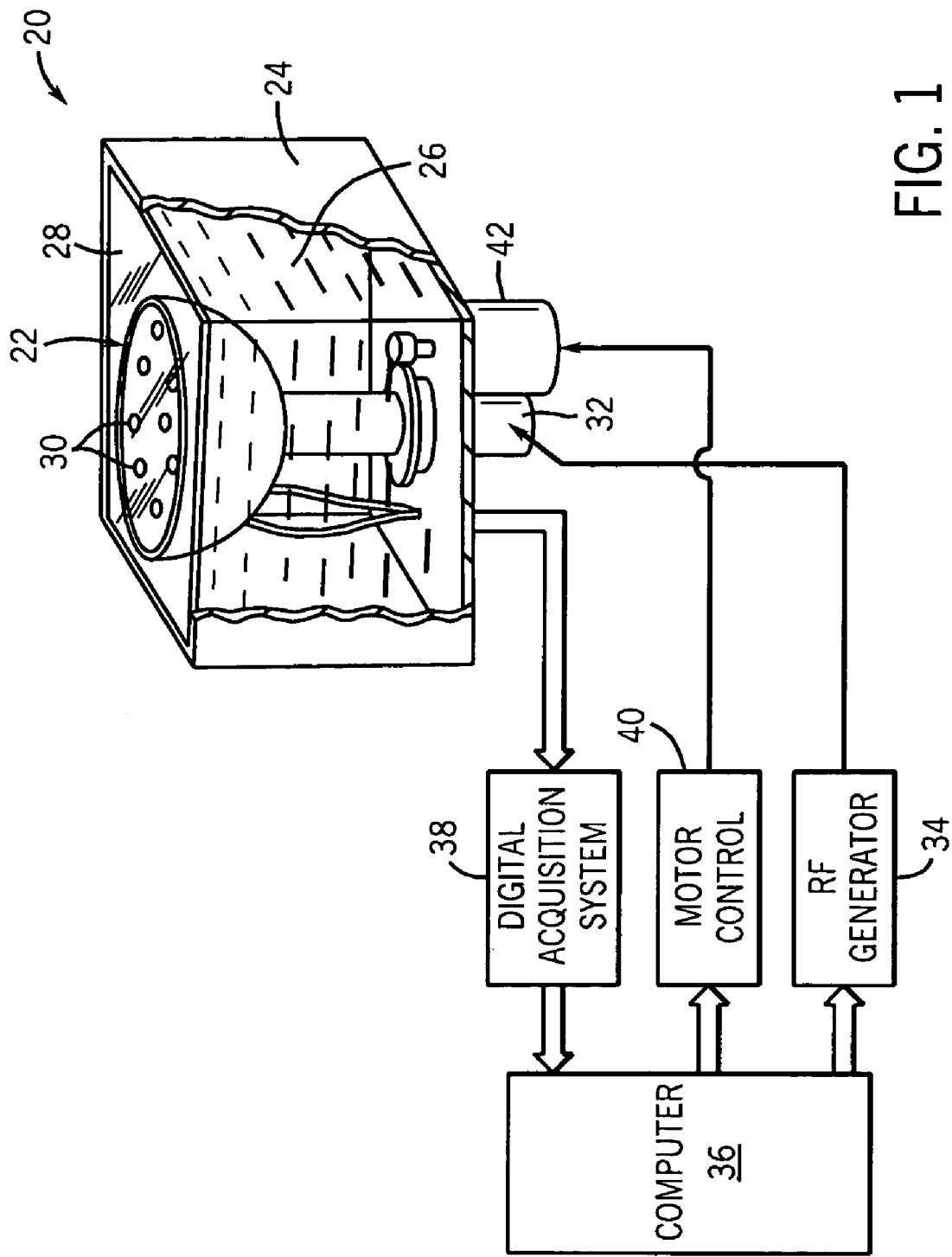
FIG. 1 is a schematic view of a TCT breast scanner in which the present invention is applicable.

Referring now to FIG. 1, a TCT breast scanner or mammography system 20 is schematically illustrated. While the present invention will be described with respect to a TCT system designed to acquire data in accordance with a mammography, one skilled in the art will appreciate that the present invention is equivalently applicable with TCT systems designed for other purposes. In one embodiment, the TCT system 20 includes an imaging bowl 22 designed to receive a human breast for TCT data acquisition. The imaging bowl 22 is preferably located within an imaging tank 24 that includes fluid or other media having dielectric and ultrasonic properties which are close to that of typical breast tissue at RF frequencies. Additionally, it is preferred that the fluid contained within tank 24 have acoustic properties similar to that of breast tissue, such as water, alcohol, or mineral oil. In one embodiment, the breast is placed directly within media 26 or, in an alternate embodiment, media 26 may be secured within tank 24 by a sheet 28 of pliable material. It is preferred that pliable sheet 28 have a relatively thin thickness and is used to provide good mechanical contact and acoustic coupling between the breast and media 26 in tank 24.

As mentioned previously, TCT imaging is predicated upon the projection of RF energy toward an imaging object such that thermal expansion occurring as a result of the reception of the radio waves causes shock waves in the imaging object that may be detected by ultrasonic transducers. It is contemplated that infrared or near-infrared energy may equivalently be used to induce thermal expansion in tissue of the imaging object. In this regard, imaging bowl 22 includes a number of ultrasonic transducers 30 that are integrated or otherwise formed therewith. To facilitate the transmission of RF or other high frequency energy toward the imaging object, a cylindrical acoustic wave guide 32 is connected to an RF generator 34 and operates as an antenna for irradiating the imaging object. In a preferred embodiment, RF generator 34 is controlled by computer 36 in such a manner as to provide short duration pulses of radiation to the breast or imaging object. Each pulse or burst of radiation causes localized heating and expansion in the energy object. The tissue heating energy may be projected in several fashions. For example, the energy may be projected impulsively in time and uniformly in space. Other examples include: periodically in time and uniformly in space, impulsively in time and selectively in space, and periodically in time and selectively in space. Based on the absorbtive characteristics of tissue in the imaging object, neighboring tissues may be distinguished from one another. For example, tumorous tissue is believed to expand relatively more rapidly and extensively than neighboring healthy tissue thereby creating an acoustic wave that will propagate through the tissue. These acoustic waves have acoustic frequencies ranging from very low to approximately the reciprocal of the electromagnetic pulse length. One skilled in the art will appreciate that the acoustic waveforms produced by RF irradiation within the breast travel through tissue at a velocity of sound propagation which is approximately 1.5 mm per microsecond. Fluid 28 fills the tank 24 to provide good ultrasound coupling between the tissue and transducers. One skilled in the art will recognize that the choice of fluid determines not only ultrasound coupling but also RF penetration properties. Furthermore, other embodiments may not require a fluid-filled tank. For instance, transducers might be placed directly on the patient's skin and RF may propagate through air, as is done in clinical magnetic resonance imaging systems.

TCT system 20 is designed to operate with several different RF frequencies, but frequencies in the range of 200 to 600 MHz are preferred. At these frequencies, energy penetration is sufficient, absorption is adequate, and the differential absorption between different types of tissue is distinguishable. Further, it has been shown that cancerous breast tissue absorbs two to five times as much RF energy than normal breast tissue once stimulated with frequencies in the range of 300 to 500 MHz. Additionally, it is believed that signal-to-noise ratio (SNR) is optimized in imaging water-containing tissues at frequencies near 434 MHz.

Transducers 30, as noted above, detect acoustic or ultrasonic waves that are generated within the imaging object by short irradiation pulses from RF generator 34. The acoustic waves travel from emission sites within the imaging object at the velocity of sound in tissue. It is preferred that the transducers be constructed so as to be most sensitive to sonic frequencies nominally below the maximum frequency stimulated by the irradiation pulse described above. Furthermore, for a three-dimensional embodiment of this invention, the transducers should have isotropic sensitivity to incoming pressure waves. On the other hand, for a two-dimensional embodiment, transducers should be focused to receive only waves originating within the imaging plane. The transducers 30 are electrically connected to a digital acquisition system 38 whereupon the data is input to computer 36 for image reconstruction.

It is contemplated that imaging bowl 22 as well as transducers 30 may be rotated during data acquisition. As such, TCT system 20 includes a motor control 48 that is driven by computer 36 so as to rotate imaging bowl 22 during the acquisition of TCT data. It is contemplated, however, that rotation of imaging bowl 22 may not be desirable for some TCT imaging protocols.

In contrast to known TCT reconstruction techniques, the present invention provides an exact inversion formula for generating a reconstruction data set from TCT data acquired from a subject. Known TCT reconstruction processes, such as Fourier-Bessel and spherical harmonic expansions, have previously been used to generate the reconstruction data set. These processes, however, result in solutions that may be characterized as an infinite series for the 2D and 3D case, respectively. In this regard, the infinite series must be truncated to provide a finite data set for reconstruction. This truncation can yield ghosting in the reconstructed image. On the other hand, the present invention provides an exact inversion formula that avoids the pitfalls associated with data truncation.

A discussion of the mathematical underpinnings of TCT imaging as well as two exemplary implementations of the present invention is set forth below.

If $p \in S^{(n-1)}$ and $f \in C_o^\infty(B_1)$, where $B_1$ is a unit ball or object centered at the origin of unit sphere S, TCT data may then be defined as the integral of f over spheres centered on the surface of the unit sphere as set forth in the following expression:

$$R_{TCT}f(p,r) = r^{n-1} \int_{o \in S^{(n-1)}} f(p+ro) do \qquad (\text{Eqn. 1})$$

where p denotes the center of spheres of radius r and $|p|=1$.

A complete data set may then be input into an inversion formula that computes $f(x)$ from measurements of $R_{TCT}f(p,r)$ data for all transducer locations. From the inversion formula it is therefore possible to recover the absorptivity function. One skilled in the art will appreciate that the definition of $R_{TCT}$, as provided in Eqn. 2, is restrictive, in that it permits only measurement of integrals centered on the surface of the unit sphere. This restriction makes computation of the adjoint and inverse operators simple. As in classical CT, the TCT adjoint operation is backprojection as demonstrated below. With TCT, however, the adjoint, $R^*_{TCT}$, is not applied directly to the data as is done in standard CT.

The TCT adjoint may be defined for any value, n, by the following expression:

$$R^*_{TCT}g(x) = \int_{|p|=1} g(p,|x-p|) dp \qquad (\text{Eqn. 2}).$$

A number of techniques may be used to derive exact inversion formulae for a complete data case. Fourier-Bessel expansion is one technique and results in a solution written as an infinite series. As described above, an infinite series solution is less than ideal as truncation of the infinite series introduces errors into the image. Therefore, an exact inversion solution analogous to ρ-filtered layergram inversion of standard x-ray CT data, as set forth in the following equation for n=3, is preferred:

$$f(x) = \frac{-1}{8\pi^2} \Delta_x \left( \int_{|p|=1} \frac{1}{|x-p|} R_{TCT} f(p, |x-p|) dp \right), \quad \text{(Eqn. 3)}$$

It should be noted that the adjoint acts upon weighted data. By defining a weighting operator as:

$$Wg(p, s) = \frac{1}{s} g(p, s), \quad \text{(Eqn. 4)}$$

then the inversion formula for n=3 may be written as:

$$f(x) = \frac{-1}{8\pi^2} \Delta_x (R^*_{TCT} W R_{TCT} f)(x). \quad \text{(Eqn. 5)}$$

Eqn. 5 differs from a standard inexact inversion formula in the appearance of the weighting function, as illustrated in the following equation which is correct for standard codim-1 CT in three dimensions, and provides approximate TCT reconstruction:

$$f(x) = \frac{-1}{8\pi^2} \Delta_x (R^* R f)(x), \quad \text{(Eqn. 6)}$$

which is akin to a CT ρ-filtered inversion formula.

Referring again to Eqn. 3, taking the derivatives of the Laplacian inside the integral yields a filtered-backprojection version:

$$f(x) = \frac{-1}{8\pi^2} \int_{|p|=1} \frac{1}{|x-p|} (R_{TCT} f)''(p, |x-p|) dp, \quad \text{(Eqn. 7)}$$

where the second derivative is taken with respect to the scalar "radius" variable and evaluated at |x-p|.

Figure 2:
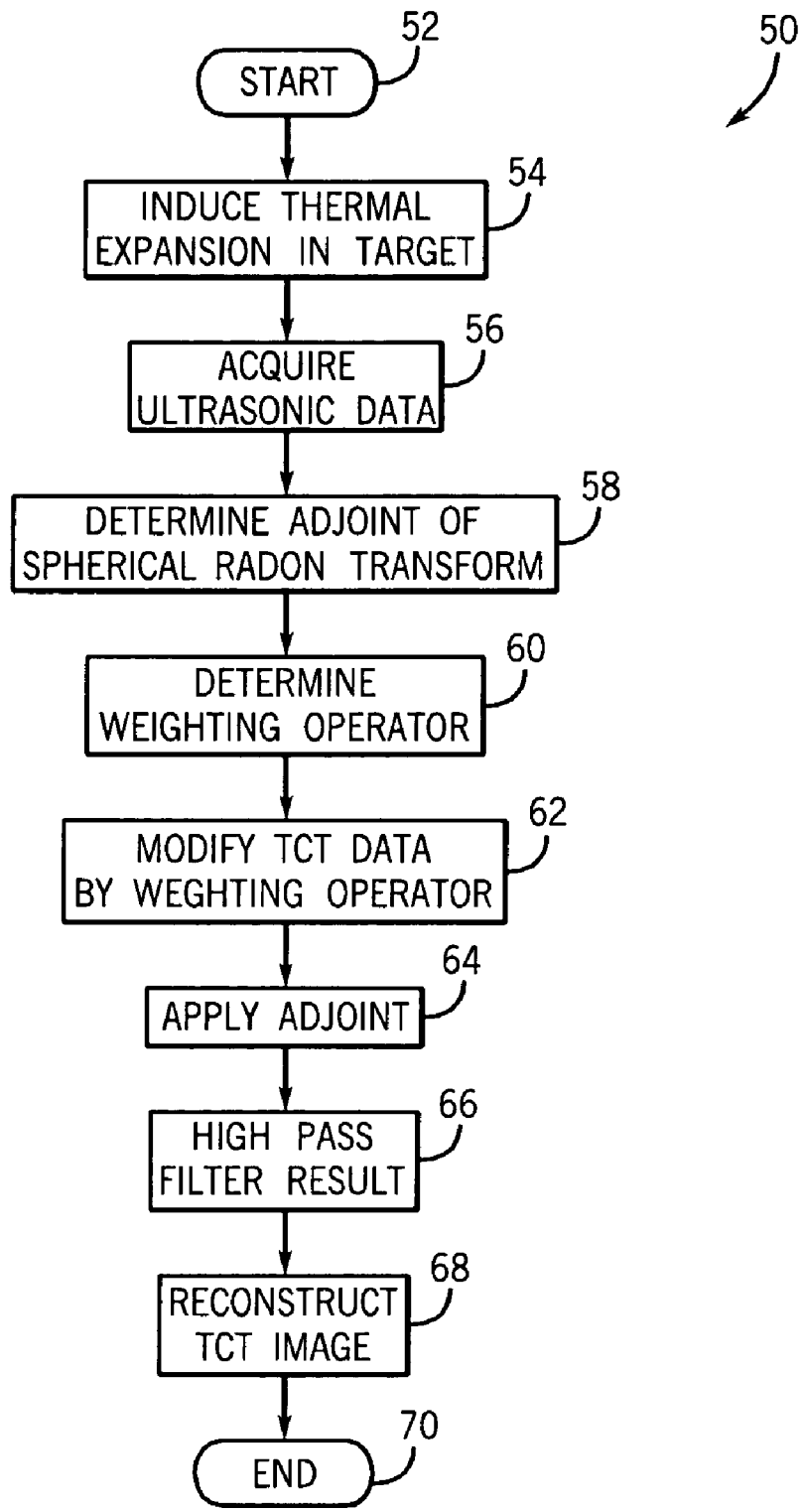
FIG. 2 is a flow chart setting forth the steps of TCT imaging in accordance with one embodiment of the invention.

Referring now to FIG. 2, the steps of a control process or algorithm for acquiring and processing TCT data according to one embodiment of the present invention will be described. As will be explained more fully below, the process 50 of FIG. 2 may be considered as a ρ-filtered reconstruction process as opposed to a filtered-backprojection reconstruction process 72 that will be described with respect to FIG. 3. The present invention may be carried out according to either reconstruction technique.

The ρ-filtered reconstruction process 50 begins at 52 with positioning of the subject in a TCT scanner, such as that described with respect to FIG. 1, and defining the scan parameters to acquire TCT data from the target subject or object. As such, at 54, the imaging process begins with the induction of thermal expansion in the target, as described with respect to FIG. 1. The thermal expansion, which may be caused by the application of RF, infrared, or near-infrared energy to the target, generates thermal expansion and subsequent compression in the target thereby causing shockwaves that may be detected ultrasonically with transducers positioned relative to the target object. Accordingly, ultrasonic data is acquired at step 56 and the adjoint of the spherical Radon transform is determined in step 58. As will be described more fully below, the adjoint will be used to modify the TCT data. A weighting operator or factor is determined at 60 in accordance with the formula set forth in Eqn. 4 above. The TCT data is then modified by first applying the weighting factor at 62 followed by application of the adjoint at 64. The weighted and modified TCT data then undergoes high-pass filtering at 66 to reconstruct a TCT image at 68 of the target whereupon the imaging process is complete 70.

Figure 3:
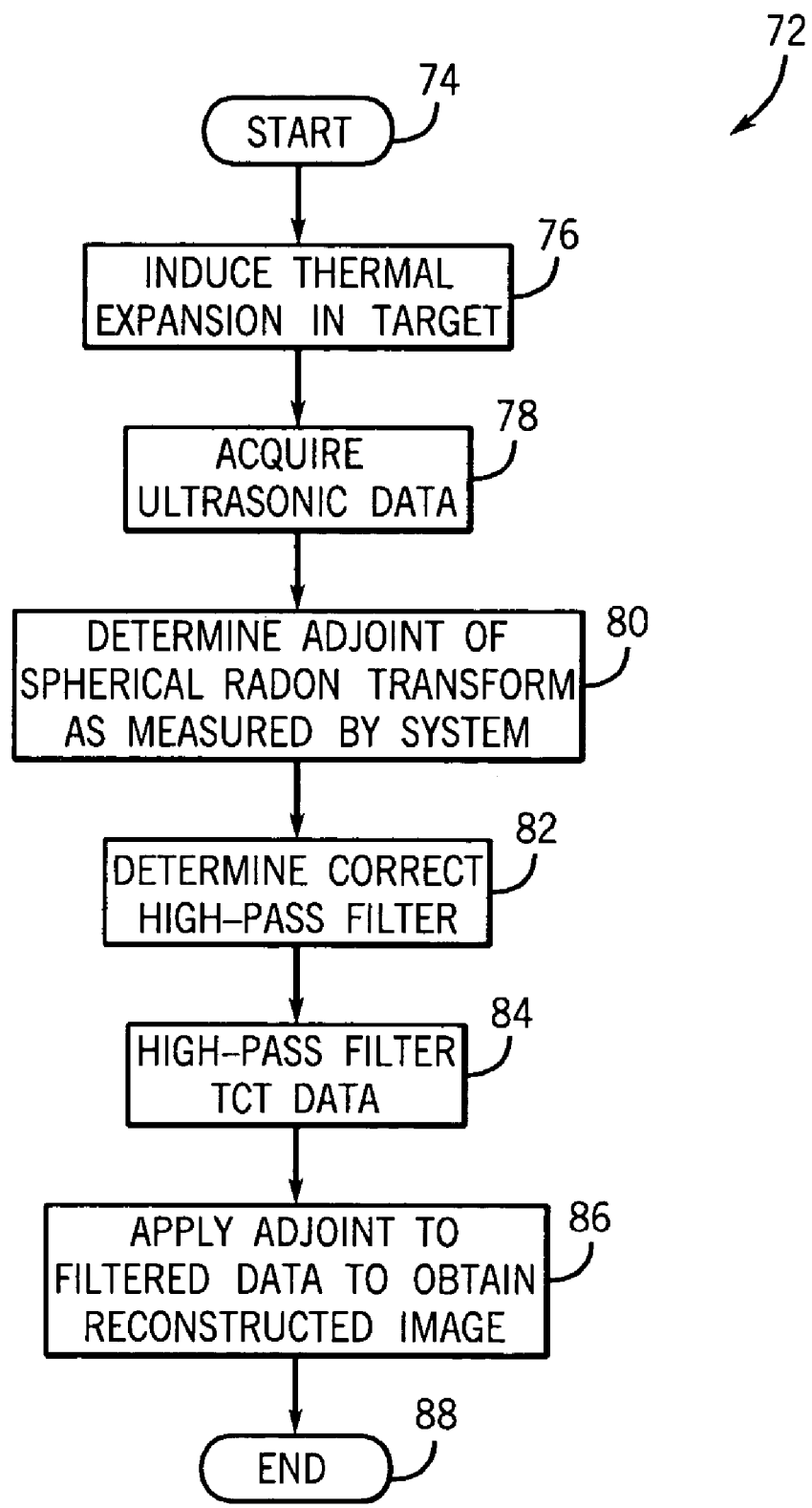
FIG. 3 is a flow chart setting forth the steps of TCT imaging in accordance with another embodiment of the invention.

In contrast and referring to FIG. 3, another embodiment of the present invention includes a filtered-backprojection reconstruction process 72. Similar to the ρ-filtered reconstruction heretofore described, the filtered back-projection process 72 begins at 74 with proper positioning of the subject within the TCT scanner, FIG. 1, and defining of the scan parameters. Thermal expansion is then induced in the target at 76 with application of RF, infrared, or near-infrared energy to the target. As described above, the application of the RF, infrared, or near-infrared energy will create shockwaves in the target that may be ultrasonically detected at 78 with an array of ultrasonic transducers positioned in relative proximity to the target. An adjoint of the spherical Radon transform as measured by the TCT system is determined at 80. With the back-projection technique 72, an appropriate high-pass filter is determined at 82. The TCT data then undergoes high-pass filtering at 84 prior to application of the adjoint and weighting operator. The weighting factor, which is determined in accordance with that described, is then applied to the filtered data at 85. The filtered and weighted TCT data is then modified by application of the adjoint at 86 to obtain a reconstructed image. The filtered back-projection technique is then complete at 88.

While it is contemplated that the heretofore described imaging techniques may be used in a number of applications, it is recognized that mammography is one modality where the present invention may be particularly applicable. Mammography is well-suited for a number of reasons. First, cross-sectional reconstructions are preferable to projection images provided by traditional x-ray. An "exact" inversion formula, as disclosed herein, is possible for the fill data case and is believed to be applicable for clinically realistic partial data sets as well. Second, ultrasonic energy is dissipated so TCT potentially can enhance the depth penetration of standard reflection ultrasonic imaging if it is possible to deposit RF, infrared, or near-infrared energy throughout the breast. Third, TCT uses no ionizing radiation. Fourth, TCT does not require compression. These are just a few of the reasons why TCT, as described herein, may be particularly applicable to mammography. One skilled in the art will readily appreciate numerous other advantages that may be achieved through application of the principles of TCT for mammographic applications as well as other targeted applications, such as small animal imaging.

Therefore, the present invention includes a method of diagnostic imaging which includes the steps of acquiring TCT data and determining an adjoint of the TCT data. The method further includes determining a weighting operator and modifying the TCT data by the adjoint and the weighting operator to generate a reconstruction data set. The method further includes the step of reconstructing an image of the object from the reconstruction data set.

A TCT imaging system includes an energy source configured to apply energy to an imaging object to induce thermal expansion in the imaging object. One or more sensors is provided to acquire ultrasonic data from the imaging object caused by energy induced thermal expansion in the imaging object. The imaging system further includes a computer programmed to apply an exact inversion to the acquired ultrasonic data to yield an image of the object.

A computer readable storage medium is disclosed and has a computer program stored thereon and represents a set of instructions that when executed by a computer causes the computer to acquire ultrasonic data resulting from application of energy to cause thermal induced displacement in an imaging object. The computer is further caused to determine an adjoint from the ultrasonic data. The computer is then caused to weight the acquired ultrasonic data by a weighting operator to form a weighted set of ultrasonic data. The adjoint is then applied to the weighted set of ultrasonic data to form a final set of ultrasonic data. The set of instructions then causes the computer to reconstruct an image from the final set of ultrasonic data by applying a high-pass filter.

The present invention has been described in terms of the preferred embodiment, and it is recognized that equivalents, alternatives, and modifications, aside from those expressly stated, are possible and within the scope of the appending claims.

What is claimed is:

1. A method of diagnostic imaging, the method comprising the steps of:
   acquiring TCT data;
   determining an adjoint of the TCT data;
   determining a weighting operator;
   modifying the TCT data by the adjoint and the weighting operator to generate a reconstruction data set that avoids data truncation; and
   reconstructing an image of a subject from the reconstruction data set, the image having reduced ghosting attributable to data truncation.

2. The method of claim 1 further comprising the step of high band-pass filtering the TCT data after the TCT data has been modified by the adjoint of a spherical Radon transform and the weighting operator that accounts for a spherical curvature in the acquired data.

3. The method of claim 2 wherein the reconstructed image is defined by:

$$f(x) = \frac{-1}{8\pi^2} \Delta_x \left( \int_{|p|=1} \frac{1}{|x-p|} R_{TCT} f(p, |x-p|) \, dp \right).$$

4. The method of claim 1 further comprising the step of high band-pass filtering the TCT data prior to modifying the TCT data by the adjoint of a spherical Radon transform and the weighting operator.

5. The method of claim 4 wherein the reconstructed image is defined by:

$$f(x) = \frac{-1}{8\pi^2} \int_{|p|=1} \frac{1}{|x-p|} (R_{TCT} f)''(p, |x-p|) \, dp$$

where $R_{TCT}$ corresponds to the acquired TCT data and $p$ corresponds to a transducer location from which the TCT data was acquired.

6. The method of claim 1 wherein the step of acquiring includes measuring ultrasonic emission of tissue in the subject resulting from application of one of RF energy, infrared, and near-infrared energy, and wherein the ultrasonic emission is relative to spheres centered about a transducer location.

7. The method of claim 6 further comprising the step of integrating energy absorption over one or more spheres centered about one or more transducer locations.

8. A TCT imaging system comprising:
   an energy source configured to apply energy to an imaging object to induce thermal expansion in the imaging object;
   one or more sensors configured to acquire ultrasonic data from the imaging object caused by energy-induced thermal expansion in the imaging object; and
   a computer programmed to apply an exact inversion to the acquired ultrasonic data to yield a reconstructed image, wherein applying the exact inversion comprises determining an adjoint of the acquired ultrasonic data, determining a weighting factor, and modifying the acquired ultrasonic data by the weighting factor and the adjoint.

9. The TCT imaging system of claim 8 wherein the computer is further programmed to high-pass filter the acquired ultrasonic data after modification by the weighting factor and the adjoint to yield the reconstructed image.

10. The TCT imaging system of claim 9 wherein the reconstructed image is defined by:

$$f(x) = \frac{-1}{8\pi^2} \Delta_x (R^*_{TCT} W R_{TCT} f)(x).$$

11. The TCT imaging system of claim 8 wherein the computer is further programmed to high-pass filter the acquired ultrasonic data before modification by the weighting factor and the adjoint to yield the reconstructed image.

12. The TCT imaging system of claim 11 wherein the computer is further programmed to back-project the ultrasonic data.

13. The TCT imaging system of claim 12 wherein the reconstructed image is defined by:

$$f(x) = \frac{-1}{8\pi^2} \int_{|p|=1} \frac{1}{|x-p|} (R_{TCT} f)''(p, |x-p|) \, dp,$$

where $x \in D$.

14. The TCT imaging system of claim 8 wherein the reconstructed image is one of a 2D and a 3D image.

15. A non-transitory computer readable storage medium having a computer program stored thereon and representing a set of instructions that when executed by a computer causes the computer to:
   acquire ultrasonic data resulting from application of energy to cause thermal-induced displacement in an imaging object;
   determine an adjoint therefrom;
   weight the acquired ultrasonic data by a weighting operator to form a weighted set of ultrasonic data;
   apply the adjoint to the weighted set of ultrasonic data to form a final set of ultrasonic data; and
   reconstruct an image from the final set of ultrasonic data.

16. The computer readable storage medium of claim 15 wherein the set of instructions further causes the computer to high-pass filter the final set of ultrasonic data to complete reconstruction.

17. The computer readable storage medium of claim 15 wherein the set of instructions further causes the computer to high-pass filter the acquired ultrasonic data prior to application of the weighting operator.

18. The computer readable storage medium of claim 15 wherein the final set of ultrasonic data includes 3D data.

19. The computer readable storage medium of claim 15 wherein the energy includes one of RF energy, infrared energy, and near-infrared energy.

20. The computer readable storage medium of claim 15 wherein the imaging object is a human breast.

21. The computer readable storage medium of claim 15 wherein the computer is caused to acquire the ultrasonic data with transducers positioned on a measurement surface.

22. The computer readable storage medium of claim 21 wherein the computer is caused to determine the adjoint of a spherical Radon transform.

23. The computer readable storage medium of claim 15 wherein the computer is caused to determine the adjoint without defining an infinite series.

* * * * *

UNITED STATES PATENT AND TRADEMARK OFFICE
CERTIFICATE OF CORRECTION

| | | |
|---|---|---|
| PATENT NO. | : 7,878,976 B2 | Page 1 of 1 |
| APPLICATION NO. | : 10/864567 | |
| DATED | : February 1, 2011 | |
| INVENTOR(S) | : Patch et al. | |

It is certified that error appears in the above-identified patent and that said Letters Patent is hereby corrected as shown below:

Title Page, (73) Assignees, delete "Corvallia"
substitute therefore -- Corvallis --.

Signed and Sealed this
Nineteenth Day of April, 2011

David J. Kappos
*Director of the United States Patent and Trademark Office*